(12) United States Patent
Nishitani et al.

(10) Patent No.: US 7,718,805 B2
(45) Date of Patent: May 18, 2010

(54) PROCESS FOR PREPARING REBAMIPIDE

(75) Inventors: Shinji Nishitani, Rockville, MD (US); Norio Fukuda, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 445 days.

(21) Appl. No.: 10/587,509

(22) PCT Filed: Nov. 30, 2005

(86) PCT No.: PCT/JP2005/022412

§ 371 (c)(1), (2), (4) Date: Jul. 27, 2006

(87) PCT Pub. No.: WO2006/059781

PCT Pub. Date: Jun. 8, 2006

(65) Prior Publication Data

US 2007/0249835 A1   Oct. 25, 2007

(30) Foreign Application Priority Data

Dec. 1, 2004   (JP) .............................. 2004-348425

(51) Int. Cl.
*C07D 215/38* (2006.01)
(52) U.S. Cl. ..................................... 546/157
(58) Field of Classification Search .................. 546/157
See application file for complete search history.

(56) References Cited

U.S. PATENT DOCUMENTS

| 4,578,381 | A | 3/1986 | Uchida |
| 6,680,386 | B2 | 1/2004 | Lee |

FOREIGN PATENT DOCUMENTS

| JP | 60-19767 | 1/1985 |
| JP | 3-145468 | 6/1991 |
| JP | 2004-131506 | 4/2004 |
| KR | 2003050412 A1 | 6/2003 |

OTHER PUBLICATIONS

Uchida, Chem Pharm Bull, vol. 33(9), pp. 3775-3786, 1985.*
Otsubo, Chem Pharm Bull, vol. 39(11), pp. 2906-2909, 1991.*
Minoru Uchida et al., "Development of Anti-ulcer Drug, Rebamipide," Journal of Synthetic Organic Chemistry, Japan vol. 53, No. 12, 1995, pp. 1077-1089.
R.J. Chudgar et al., "Studies in the Synthesis of Quinoline Derivatives: Part I: Synthesis of Bromoquinolines," Jour. Indian Chem. Soc, vol. 46, No. 6, 1969.
Minoru Uchida et al., "Studies on 2(1H-Quinolinone Derivatives as Gastric Antiulcer Active Agents, 2-(4-Chlorobenzoylamino)-3-[2(1H)-Quinolinon-4-yl]propionic Acid and Related Compounds," Chem. Pharm. Bull., vol. 33, No. 9, 1985, pp. 3775-3786.

* cited by examiner

*Primary Examiner*—D. Margaret Seaman
(74) *Attorney, Agent, or Firm*—Finnegan, Henderson, Farabow, Garrett & Dunner, L.L.P.

(57) ABSTRACT

The invention provides an improved process for preparing rebamipide that is useful as a medicament, which makes it possible to prepare rebamipide with high purity and high yield. The invention is an improved process for preparing rebamipide of the formula (1), comprising subjecting a carbostyril amino acid compound of the formula (5) or a salt thereof containing a compound of the formula (11) as an impurity to a reduction treatment in the presence of hydrogen and a catalyst in a basic aqueous solution, thereby selectively reducing the impurity compound (11) to transform into the carbostyril amino acid compound (5); and then acylating the compound (5) in a basic aqueous solution to give rebamipide (1).

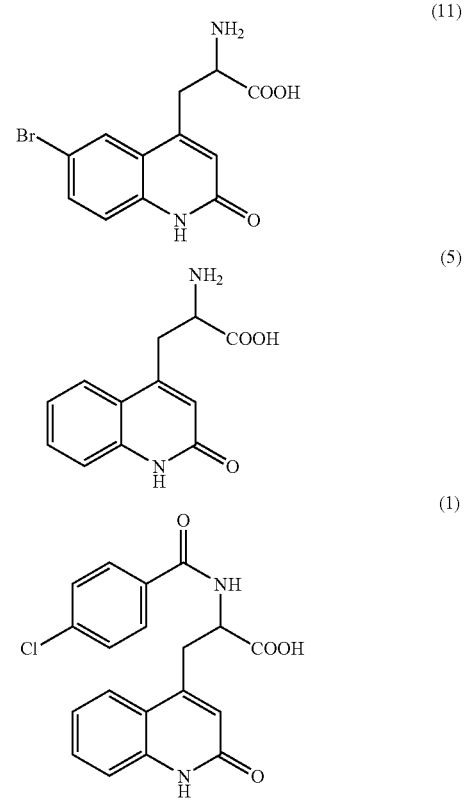

1 Claim, No Drawings

PROCESS FOR PREPARING REBAMIPIDE

TECHNICAL FIELD

The invention relates to an improved process for preparing rebamipide that is useful as a medicament for treating gastric ulcer and the like, which makes it possible to prepare rebamipide with high purity and high yield.

BACKGROUND ART

Rebamipide, which means a carbostyril compound (chemical name: 2-(4-chlorobenzoylamino)-3-[2(1H)-quinolon-4-yl]propionic acid) of the following formula (1), is a medicament that has a potent effect on the treatment of gastric ulcer, acute gastritis, or gastric mucosa lesion affected in acute exacerbation of chronic gastritis.

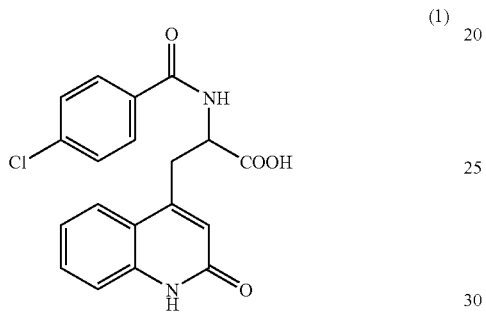

(1)

As an example of the process for preparing rebamipide, a process shown in the following scheme 1 is known (JP-A-60-19767). The process is illustrated as follows:

That is, bromomethyl carbostyril (2) is reacted with diethylacetamide malonate (3) in the presence of a base such as sodium ethoxide to give carbostyril malonate compound (4);

the compound (4) is hydrolyzed and decarboxylated in the presence of a mineral acid such as hydrochloric acid to prepare carbostyril amino acid compound (5); and then the compound (5) is acylated with 4-chlorobenzoyl chloride (6) to prepare the desired rebamipide of the formula (1).

Scheme 1

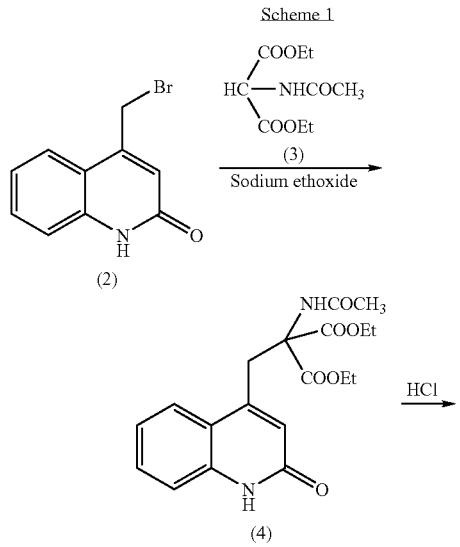

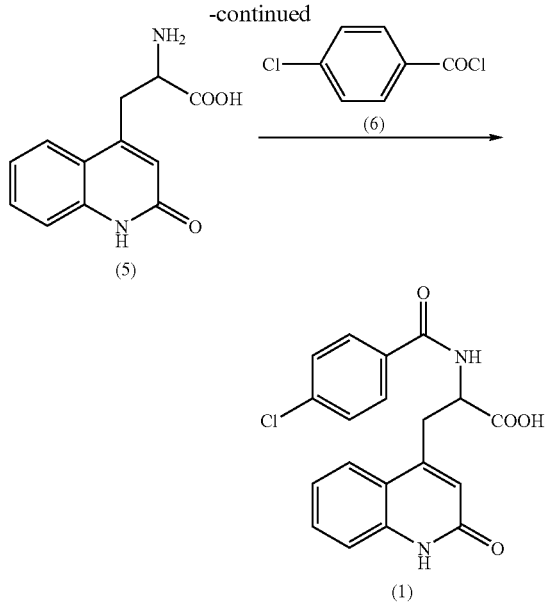

The above starting material, bromomethyl carbostyril (2), can be prepared, for example, as shown in the following scheme 2:

That is, acetoacetanilide (7) is brominated with bromine, N-bromosuccinimide, or the like to give a compound of the formula (8); and then the compound (8) is ring-closed with a condensing agent such as concentrated sulfuric acid to prepare the compound (2). However, the product (2) contains 6-bromocarbostyril compound of the following formula (9) as an impurity, which is one of by-products produced from the above bromination.

Scheme 2

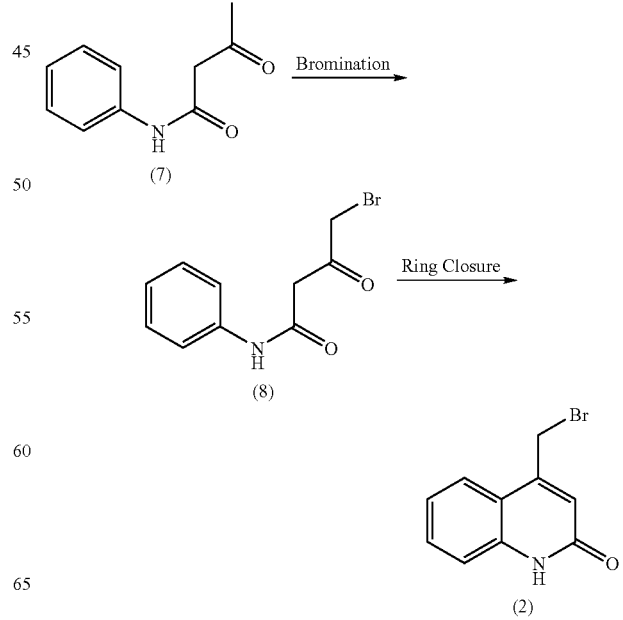

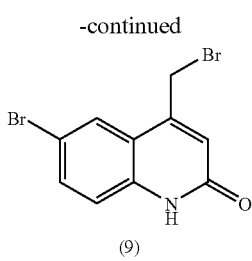

On transforming the bromomethyl carbostyril (2) to rebamipide (1) according to the above scheme 1, the above impurity contained in the bromomethyl carbostyril (2), i.e. 6-bromocarbostyril compound (9), is reacted in the same behavior of the bromomethyl carbostyril (2), as shown in the following scheme 3, to give the corresponding 6-bromo compound of the formula (12) via the corresponding compounds of the formula (10) and formula (11), and thereby the impurity (12) is contained in the desired rebamipide (1).

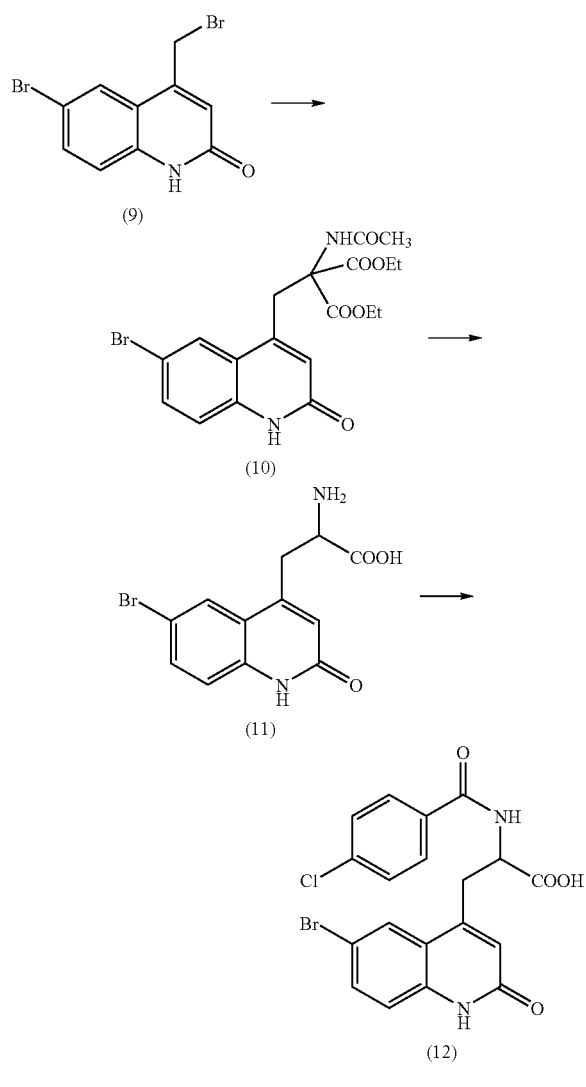

It is possible to partly decrease the amount of the produced impurity 6-bromocarbostyril compound (9) by controlling the condition of the bromination shown in the above-mentioned scheme 2, for example, engaging an equimolar or less amount of used bromine to the amount of the acetoacetanilide (7) and making the reaction temperature 50° C. or less, however, it might be limitative to decrease the preparation of the 6-bromocarbostyril compound (9) without significantly decreasing the yield of the desired bromocarbostyril (2) by only controlling the reaction condition.

Accordingly, it is necessary to remove such contaminated impurity 6-bromo compound (12) when the desired rebamipide (1) is used as a medicament, however, it is difficult to prepare rebamipide with high purity and high yield since such removal is really difficult, and the impurity is not fully removed by recrystallizing or washing with solvent, and additionally it is accompanied with loss of the desired rebamipide by the operation. From such viewpoint, it started to study the removal of the 6-bromocarbostyril compound (9) contained in the bromomethyl carbostyril (2).

Thus, the method of removing the contaminated impurity 6-bromocarbostyril compound (9) from the bromomethyl carbostyril (2) includes, for example, recrystallizing from various solvents and dispersing/washing with various solvents; however, such methods do not provide any sufficient effect of the removal. Also, for example, using N,N-dimethyl formamide, N,N-dimethyl acetamide, 1-methyl-2-pyrrolidone and the like, a certain effect of the removal will be observed; however, in this case the bromomethyl carbostyril (2) will be lost a lot due to transference into the filtrate. Accordingly, such method is also not useful in fact.

Additionally, if the derivatives of the contaminated impurity 6-bromo compound is tried to be removed as the following steps: that is, removing the corresponding 6-bromo compound (10) from carbostyril malonate compound (4) in the above-mentioned scheme 1, or removing the corresponding 6-bromo compound (11) from the carbostyril amino acid compound (5) in the same scheme, the same problem will arise.

DISCLOSURE OF INVENTION

Problem to be Solved by the Invention

Thus, the present inventors have extensively studied which step in the procedure is effective to remove the contaminated impurity 6-bromo compound, and have found that the desired rebamipide could be prepared with high purity and high yield by subjecting the carbostyril amino acid compound (5) containing the 6-bromocarbostyril amino acid compound (11) as an impurity to a reduction treatment just before converting compound (5) into the desired rebamipide by the acylation, thereby selectively reducing only the compound (11) to transform into the useful carbostyril amino acid compound (5); and then acylating the produced compound (5). Based upon the new findings, the present invention has been completed.

An object of the present invention is to provide an improved process for preparing rebamipide that is useful as a medicament, which makes it possible to prepare rebamipide with ease, high purity and high yield.

Another object of the present invention is to provide a method of effectively removing the 6-bromo compound produced as a by-product in the process for preparing rebamipide.

More another object of the present invention is to provide a method of preparing the desired rebamipide with higher purity and higher yield in the step from the bromomethylcarbostyril (2) to the desired rebamipide (1) through the removal of the impurity by selectively reducing the 6-bromocarbostyril amino acid compound (11) contained as an impurity in the carbostyril amino acid compound (5) just before the acylation, to transform into the useful carbostyril amino acid compound (5); and then acylating the produced compound (5).

MEANS TO SOLVE THE PROBLEM

According to the present invention, the desired rebamipide (1) can be prepared by subjecting the carbostyril amino acid compound (5) or the salt thereof containing the 6-bromocarbostyril amino acid compound (11) as an impurity to a reduction treatment in the presence of hydrogen and a catalyst in a basic aqueous solution, thereby selectively reducing only the impurity compound (11) to transform into the carbostyril amino acid compound (5); and then acylating the carbostyril amino acid compound (5) with 4-chlorobenzoyl chloride in a basic aqueous solution. The method of the invention is shown in the following scheme 4.

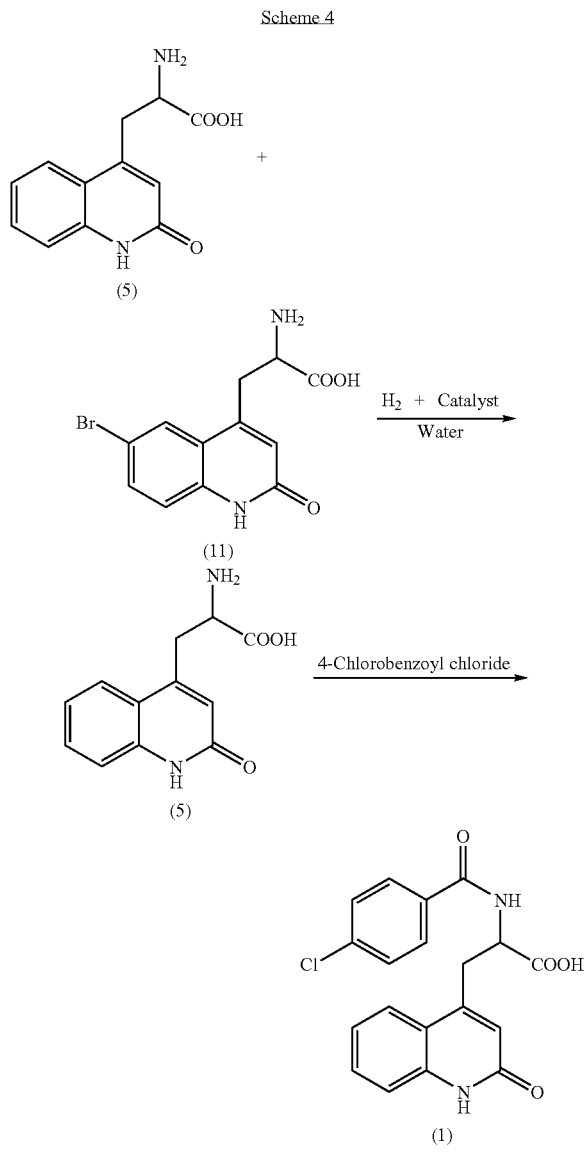

The process of the invention is not a conventional method of removing impurities such as recrystallization using a solvent, dispersing/washing, and column chromatography; but a purification method through reduction wherein the desired compound itself is not reduced, but the impurity contained in the desired compound is reduced to be transformed into the desired compound; and thereby the purity of the product is enhanced. Using such unconventional purification method, the desired rebamipide can be prepared in higher yield.

BEST MODE FOR CARRYING OUT THE INVENTION

The example of a salt of the carbostyril amino acid compound (5) containing the 6-bromocarbostyril amino acid compound (11) as an impurity, used herein, includes a mineral acid salt such as hydrochloride, sulfate, hydrobromide and the like; and an alkali metal salt such as sodium salt, lithium salt and the like.

In order to carry out the invention, water and a basic compound is added to the carbostyril amino acid compound (5) or a salt thereof containing the impurity 6-bromocarbostyril amino acid compound (11) to prepare a basic aqueous solution. The water added herein is generally about 5-50 parts by weight to 1 part by weight of the carbostyril amino acid compound (5) or a salt thereof containing the impurity.

The examples of the basic compound which is added to basify the aqueous solution include, for example, a mineral basic compound such as sodium hydroxide, potassium hydroxide, lithium hydroxide, sodium carbonate, potassium carbonate, and lithium carbonate, which is preferably added so that the pH of the aqueous solution may exhibit below 14. However, when the carbostyril amino acid compound (5) containing the impurity is transformed into a metal salt thereof with, for example, sodium salt, potassium salt, and lithium salt, then it is not necessary to add an additional basic compound due to the basicity of the aqueous solution.

The examples of the catalyst in the invention which is used to subject the impurity 6-bromocarbostyril amino acid compound (11) to the selective reduction, include palladium catalysts and nickel catalysts, preferably Raney nickel catalyst. The amount of the used catalyst is generally about 0.01-0.50 parts, preferably about 0.02-0.20 parts by weight to 1 part by weight of the carbostyril amino acid compound (5) or a salt thereof containing the impurity.

The reduction of the invention is carried out generally at atmospheric pressure to 10 atm, preferably at atmospheric pressure to 4 atm, and generally at 0-40° C., preferably at 10-30° C. This reduction will be effectively advanced if using stirring.

After completing the reduction, the catalyst is removed off, a filtrated basic solution of the carbostyril amino acid compound (5) is reacted with 4-chlorobenzoyl chloride to give the desired rebamipide (1). The above reaction can be easily carried out according to a conventional method, for example, via Schotten-Baumann reaction.

The amount of 4-chlorobenzoyl chloride used in the above acylation is an equimolar, preferably an equimolar to 2 moles, to 1 mole of the carbostyril amino acid compound (5).

In the acylation, to a basic solution of the carbostyril amino acid compound (5) prepared by removing the catalyst, an additional basic compound (for example, sodium hydroxide, potassium hydroxide, sodium carbonate, potassium carbonate, sodium hydrogen carbonate, potassium hydrogen carbonate, sodium and the like) may be optionally added, and then 4-chlorobenzoyl chloride itself or a solution of 4-chlorobenzoyl chloride in an organic solvent such as acetone, acetonitrile, and ethyl acetate is added, and the resulting reaction can be carried out at about −10° C. to 100° C., preferably about 0° C. to 36° C., for about 5 minutes to 15 hours.

EXAMPLE

Hereinafter, the present invention is further illustrated by example.

Example 1

To 10 g of 2-amino-3-[2(1H)-quinolon-4-yl]propionic acid monohydrochloride dihydrate (the compound of the formula (5), purity by HPLC analysis: 98.56%) containing 2-amino-3-[6-bromo-2(1H)-quinolon-4-yl]propionic acid (the compound of the formula (11), percentage by HPLC analysis: 1.09%) as an impurity, 200 mL of water and 10 mL of 25% aqueous sodium hydroxide were added, and the mixture was dissolved. To the solution, 2 g of 50% water-contained Raney nickel catalyst was added and stirred under 2 atm of hydrogen for 2 hours at room temperature, and then the catalyst was filtrated off. After 2 hour-stirring, a HPLC analysis indicated that the amount of 2-amino-3-[6-bromo-2(1H)-quinolon-4-yl]propionic acid (the compound of the formula (11)) was 0.01% and the amount of 2-amino-3-[2(1H)-quinolon-4-yl]propionic acid (the compound of the formula (5)) was 99.73%. After adding 10 mL of 25% aqueous solution of sodium hydroxide to the catalyst-removed solution, a solution of 10 g of 4-chlorobenzoyl chloride in 50 mL of acetone was added thereto dropwise under ice temperature. After the addition, the reaction mixture was allowed to be acidified with hydrochloric acid and the resultant crystal was filtrated. The crystal washed with water and acetone, and air-dried at about 80° C. to give 11.7 g of rebamipide (1) (yield: 96.2%, purity by HPLC analysis: 99.60%).

INDUSTRIAL APPLICABILITY

The invention provides a highly effective purification method without loss of the desired compound, by converting the contaminated impurity 6-bromo compound, which is hardly removed by a conventional purification method, into the desired compound by selective reduction thereof and thereby the purity of the whole desired compound can be enhanced. Accordingly, the method of the invention might be advantageously used in the industrial process for preparing rebamipide to be used as a medicament in which higher purity is required.

According to the method of the invention, the desired compound can easily be produced on industrial scale by easy operation since water may be used as a solvent for the reduction and the reaction may be carried out under a mild condition for relatively short time. Furthermore, after completion of the reduction in the former step, the basic aqueous solution obtained by removing the catalyst can be used in the next acylation step without further treatment, and hence the invention will be so useful to produce the desired rebamipide with high yield on large scale.

The invention claimed is:
1. A process for preparing rebamipide of the formula (1):

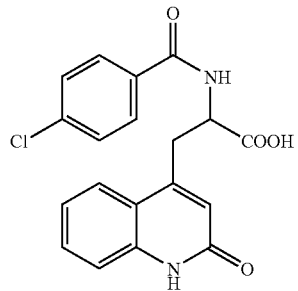

comprising:
subjecting a carbostyril amino acid compound of the formula (5):

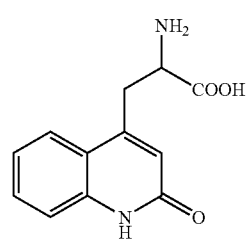

or a salt thereof
containing a 6-bromocarbostyril amino acid compound of the formula (11):

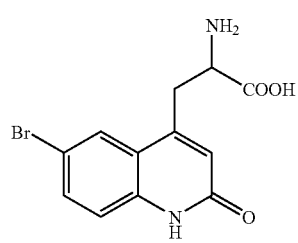

as an impurity to a reduction treatment in the presence of hydrogen and a catalyst in a basic aqueous solution, thereby selectively reducing the impurity compound (11) to transform into the carbostyril amino acid compound (5); and then
reacting the carbostyril amino acid compound (5) with 4-chlorobenzoyl chloride in a basic aqueous solution to give rebamipide (1).

* * * * *